(12) United States Patent
Vogt et al.

(10) Patent No.: US 8,757,866 B2
(45) Date of Patent: Jun. 24, 2014

(54) DEVICE FOR MIXING AND DISPENSING BONE CEMENT

(75) Inventors: Sebastian Vogt, Erfurt (DE); Hubert Buechner, Reinheim (DE)

(73) Assignee: Heraeus Medical GmbH, Wehrheim (DE)

( * ) Notice: Subject to any disclaimer, the term of this patent is extended or adjusted under 35 U.S.C. 154(b) by 813 days.

(21) Appl. No.: 12/824,310

(22) Filed: Jun. 28, 2010

(65) Prior Publication Data

US 2010/0329074 A1 Dec. 30, 2010

(30) Foreign Application Priority Data

Jun. 29, 2009 (DE) .......................... 10 2009 031 178

(51) Int. Cl.
| | | |
|---|---|---|
| B01F 13/06 | (2006.01) | |
| B01F 15/02 | (2006.01) | |
| A61B 17/58 | (2006.01) | |
| A61B 17/60 | (2006.01) | |
| A61F 2/00 | (2006.01) | |
| B67D 7/76 | (2010.01) | |

(52) U.S. Cl.
USPC ........ 366/190; 366/139; 366/163.1; 366/189; 366/195; 366/602; 606/92; 606/94; 222/190

(58) Field of Classification Search
None
See application file for complete search history.

(56) References Cited

U.S. PATENT DOCUMENTS

| | | |
|---|---|---|
| 3,195,778 A | 7/1965 | Coates |
| 4,671,263 A | 6/1987 | Draenert |
| 4,758,096 A | 7/1988 | Gunnarsson |
| 4,973,168 A | 11/1990 | Chan |
| 5,100,241 A | 3/1992 | Chan |
| 5,344,232 A | 9/1994 | Nelson et al. |
| 5,551,778 A | 9/1996 | Hauke et al. |
| 5,586,821 A | 12/1996 | Bonitati et al. |

(Continued)

FOREIGN PATENT DOCUMENTS

| | | |
|---|---|---|
| DE | 36 40 279 A1 | 6/1987 |
| EP | 0 692 229 A1 | 1/1996 |

(Continued)

OTHER PUBLICATIONS

Office Action issued Oct. 16, 2013 in AU Application No. 2010202244.

(Continued)

*Primary Examiner* — Jill Warden
*Assistant Examiner* — Julie Tavares
(74) *Attorney, Agent, or Firm* — Panitch Schwarze Belisario & Nadel LLP

(57) ABSTRACT

A device (10) for mixing and dispensing bone cement includes a mixing cylinder (20), in which a mixing plunger (21) is arranged, the mixing plunger (21) being axially movable by an actuation rod (50) guided out in a sealed manner at a first cylinder end (30). A sealing plunger (42) is arranged in a region of the first cylinder end (30), is axially movable on the actuation rod (50) and seals the mixing cylinder (20) in a gas-tight manner. A sterilization plunger (41) is arranged in the region of the first cylinder end (30) between the mixing plunger (21) and the sealing plunger (42), is axially movable on the actuation rod (50) separately from the sealing plunger (42), and seals the mixing cylinder (20) in a gas-permeable manner. The sterilization plunger (41) and the sealing plunger (42) form a two-part plunger system (40).

14 Claims, 3 Drawing Sheets

(56) References Cited

U.S. PATENT DOCUMENTS

| | | | |
|---|---|---|---|
| 5,624,184 A | 4/1997 | Chan | |
| 6,033,105 A | 3/2000 | Barker et al. | |
| 6,488,651 B1 | 12/2002 | Morris et al. | |
| 6,709,149 B1* | 3/2004 | Tepic | 366/139 |
| 2006/0274601 A1* | 12/2006 | Seaton, Jr. | 366/139 |
| 2007/0211563 A1* | 9/2007 | De Vries | 366/139 |
| 2007/0217282 A1* | 9/2007 | Lidgren et al. | 366/108 |
| 2008/0037365 A1* | 2/2008 | Axelsson et al. | 366/163.1 |

FOREIGN PATENT DOCUMENTS

| | | | |
|---|---|---|---|
| EP | 1 005 901 A2 | 6/2000 | |
| EP | 1 016 452 A2 | 7/2000 | |
| EP | 1 120 167 A2 | 8/2001 | |
| EP | 1 920 738 A2 | 5/2008 | |
| JP | 2008-044372 A | 2/2008 | |
| JP | 2008-503317 A | 2/2008 | |
| WO | 94/26403 A1 | 11/1994 | |
| WO | 99/67015 A1 | 12/1999 | |

OTHER PUBLICATIONS

English translation of an Office Action issued Dec. 2, 2013 in JP Application No. 2010-144570.

* cited by examiner

DEVICE FOR MIXING AND DISPENSING BONE CEMENT

BACKGROUND OF THE INVENTION

The invention relates to a device for mixing and dispensing bone, the device having a mixing cylinder, in which a mixing plunger is arranged, whereby the mixing plunger is axially movable by an actuation rod guided out in a sealed manner at a first cylinder end, and having a sealing plunger that is arranged in a region of the first cylinder end, is axially movable on the actuation rod and seals the mixing cylinder in a gas-tight manner. Moreover, the invention relates to a bone cement system having a device for mixing and dispensing bone cement as above, a reservoir for a binding agent, in particular a monomer, and a base, whereby the base stores the device and the reservoir.

Polymethylmethacrylate (PMMA) bone cements are based on the groundbreaking work of Sir Charnley (Charnley, J., "Anchorage of the femoral head prosthesis of the shaft of the femur," *J. Bone Joint Surg.*, 42: 28-30 (1960)). PMMA bone cements consist of a liquid monomer component and a powder component. The monomer component generally contains the monomer, methylmethacrylate, and an activator (N,N-dimethyl-p-toluidine) dissolved therein. The powder component, which is also called bone cement powder, comprises one or more polymers that are made by polymerization, preferably suspension polymerization, based on methylmethacrylate and co-monomers, such as styrene, methylacrylate or similar monomers, a radio-opaquer, and the initiator, dibenzoylperoxide. When mixing the powder component with the monomer component, swelling of the polymers of the powder component in the methylmethacrylate leads to the formation of a dough that can be shaped plastically, corresponding to the actual bone cement. When mixing the powder component with the monomer component, the activator, N,N-dimethyl-p-toluidine, reacts with dibenzoylperoxide while forming radicals. The radicals thus formed trigger the radical polymerization of the methylmethacrylate. Upon advancing polymerization of the methylmethacrylate, the viscosity of the cement dough increases until the cement dough solidifies.

Polymethylmethacrylate bone cements can be mixed in suitable mixing beakers with spatulas by mixing the cement powder with the monomer liquid. This procedure is disadvantageous in that inclusions of air may be present in the cement dough thus formed and may later cause destabilization of the bone cement. For this reason, it is preferable to mix bone cement powder with the monomer liquid in vacuum mixing systems, since mixing in a vacuum removes inclusions of air from the cement dough all but completely and attains optimal cement quality (Breusch, S. J. et al., "Der Stand der Zementiertechnik in Deutschland [The State of Cementing Technology in Germany]," *Z. Orthop.*, 137: 101-07 (1999)). Bone cements mixed in a vacuum have substantially lower porosity and thus show improved mechanical properties. A large number of vacuum cementing systems have been disclosed of which the following shall be named for exemplary purposes: U.S. Pat. Nos. 6,033,105; 5,624,184; 4,671,263; 4,973,168; 5,100,241; 5,586,821; and 5,344,232; International patent application Publication Nos. WO 99/67015 A1 and WO 94/26403 A1; European patent application publication Nos. EP 1 020 167 A2; EP 1 016 452 A2; EP 0 692 229 A1; and EP 1 005 901 A2; and German published patent application DE 36 40 279 A1. European patent application No. EP 1 920 738 A2 also describes a vacuum cementing system by which bone cements can be produced.

A further development of the aforementioned are cementing systems in which both the cement powder and the monomer liquid are already packed in separate compartments of the mixing systems and are mixed with each other in the cementing system only right before application of the cement (EP 0 692 229 A1). A significant problem of these systems is the sterilization of the entire system including the cement powder and the previously sterile-filtered monomer liquid. A particular problem in this context is the procedure of sterilization with ethylene oxide which is in common use for bone cements. Compared to sterilization with gamma radiation, this sterilization method is advantageous in that the polymers contained in the cement powder are not degraded and the properties of the cement remain unaffected by the ethylene oxide sterilization. A problem that is associated with ethylene oxide sterilization is that the gaseous agent first needs to penetrate into the cartridge and/or cement reservoir container and thus into the cement powder and then needs to diffuse out of the cartridge after sterilization is complete. Accordingly, it is obligatory for the gas exchange between the interior of the cartridge and/or the reservoir container and the surroundings to be as unimpeded as possible. In contrast, the ready-for use mixing system must be sealed sufficiently tightly for preparation-by-mixing of the cement in a vacuum to be feasible.

This conflict is resolved in mixing systems that are on the market in that a lid having a porous disc is screwed onto the cement cartridge and needs to be removed right before application of the cement. In place of the lid, a vacuum-tight cartridge head is screwed on, which contains a mixing device, a vacuum connection, and an opening for the dispensing tube to be attached later. The medical user therefore needs to open and then re-close the cementing system right before preparation-by-mixing of the cement. This may cause germs, etc., to enter into the previously disinfected bone cement powder.

BRIEF SUMMARY OF THE INVENTION

It is an object of the present invention to create a device for mixing and dispensing bone cement in which the aforementioned disadvantages are eliminated, in particular in which contamination of the disinfected bone cement powder is prevented.

This object is proposed to be achieved by a device for mixing and dispensing bone cement, as set forth at the outset, characterized in that a sterilization plunger is arranged in the region of the first cylinder end between the mixing plunger and the sealing plunger, is axially movable on the actuation rod separately from the sealing plunger, and seals the mixing cylinder in a gas-permeable manner, whereby the sterilization plunger and the sealing plunger form a two-part plunger system. Moreover, the object is proposed to be achieved by a bone cement system, as set forth at the outset, wherein the base comprises a coupling element for a non-positive and/or positive fit connection to the device, in particular to a dispensing opening of the device. In this context, features and details that are disclosed in relation to the device shall obviously also apply to the bone cement system according to the invention, and vice versa.

The device according to the invention proposes to have an axially movable two-part plunger system arranged in the region of the first cylinder end, wherein the plunger system comprises a sterilization plunger and a sealing plunger, the sterilization plunger and the sealing plunger are separately axially movable on the actuation rod, the sterilization plunger seals the mixing cylinder in a gas-permeable manner, and the sealing plunger seals the mixing cylinder in a gas-tight manner.

The sterilization plunger is arranged on the actuation rod between the mixing plunger and the sealing plunger. This arrangement of the two parts of the plunger system ensures that a sterilization agent can flow into the mixing cylinder without being prevented from doing so by the sealing plunger. Only subsequently, the sealing plunger is placed on the sterilization plunger, and the two-part plunger system is thereby combined.

The core of the invention described herein is to seal one end of the mixing cylinder with a two-part plunger system. The two parts of the plunger system can be shifted axially on the actuation rod independent of each other. The sterilization plunger seals the mixing cylinder in a gas-permeable manner. Accordingly, a sterilization agent can flow into the mixing cylinder and sterilize the bone cement powder stored therein. The sealing plunger of the plunger system then allows for gas-tight sealing of the mixing cylinder in order to connect the same to a vacuum and to aspirate a binding agent for the bone cement powder into the mixing plunger. Preferably, the two-part plunger system is characterized in that the sterilization plunger seals the mixing cylinder in a gas-permeable manner, in order to allow a bone cement powder to be rinsed by a sterilization agent, and the sealing plunger seals the mixing cylinder in a gas-tight manner, in order to allow the bone cement powder to be rinsed by a binding agent, in particular a monomer.

The special feature is, on the one hand, that a gas-permeable area, that is as large as possible, is present in the cement mixing system to allow ethylene oxide to flow in for sterilization and to allow the gas to exit after completed sterilization, and, on the other hand, that a vacuum-tight seal is present to allow the preparation-by-mixing of the bone cement in the sealed cartridge to proceed in a vacuum. The plunger system can simultaneously be used as a plunger for dispensing the mixed cement from the cartridge. Accordingly, the two-part plunger system has three advantages: first, it enables disinfection of the bone cement powder with a gaseous fluid; because the mixing cylinder is sealed by the sterilization plunger. Second, the sealing plunger is used to seal the sterilization plunger. This renders feasible a mixing of the bone cement powder with a binding agent, in particular a monomer, in a vacuum. Third, the plunger system comprising a sealing plunger and a sterilization plunger is used by pushing it into the mixing cylinder and thus pressing the bone cement from the same.

In the scope of the invention, the sealing plunger is intended to seal the mixing cylinder in a gas-tight manner. This means that the sealing plunger seals the mixing cylinder with respect to the pressures that occur during mixing and are known to the person skilled in the art. The vacuum introduced into the mixing cylinder by a vacuum pump shall be reduced no more than an insignificant extent by possible leakage of the sealing plunger with respect to the mixing cylinder. In the scope of the invention, the term "gas-permeable" means that a gaseous sterilization fluid can flow through the sterilization plunger into the mixing cylinder. The sterilization plunger preferably comprises a gas-permeable grid that allows particles smaller than 5 µm to pass through. Larger particles should not to be allowed to pass through into the interior of the mixing cylinder by the gas-permeable sterilization plunger.

One advantageous embodiment of the device according to the invention is characterized in that the two-part plunger system surrounds the actuation rod. In this context, it has proven to be particularly advantageous to have the plunger system and/or the sterilization plunger and/or the sealing plunger designed to be cylinder-like in shape. Arranging the plunger system about the actuation rod facilitates easy and reversible shifting of the sealing plunger onto or away from the sterilization plunger. In a sterilization position, the sterilization plunger is arranged in the mixing cylinder, whereas the sealing plunger is arranged outside of the mixing cylinder, but on the actuation rod. This ensures that a sterilization agent can flow unimpeded into the interior of the mixing cylinder. In a mixing situation, the sealing plunger is applied onto the sterilization plunger such that the plunger system is arranged to be together. The sealing plunger prevents the vacuum present in the interior of the mixing cylinder from being reduced.

In order to produce a non-positive and/or positive fit connection between the sealing plunger and the sterilization plunger, it has proven to be preferable if the sealing plunger can be plugged onto the sterilization plunger. Both plungers of the plunger system can have corresponding clip connections, such that the sterilization plunger can be plugged onto the sealing plunger. This clip connection can be designed to be reversibly separable in order to render feasible multiple applications of the sterilization plunger.

One special feature of the device according to the invention is that subdividing the plunger system into a sealing plunger and a sterilization plunger allows not only the bone cement powder to be disinfected without attendant problems and without risk of contamination, but also renders feasible dispensing of the ready-made bone cement with the two-part plunger system. Accordingly, it has proven to be advantageous if the plunger system can be pushed axially into the mixing cylinder in order to dispense a bone cement prepared by mixing from the bone cement powder and the binding agent, in particular the monomer, through a dispensing opening. The dispensing opening is situated at a second cylinder end of the mixing cylinder. The second cylinder end is situated opposite from the first cylinder end. During dispensing, the plunger system is pushed from the direction of the first cylinder end in the direction of the second cylinder end and, in the process, presses the ready-mixed bone cement out through the dispensing opening.

In an advantageous embodiment, the dispensing opening comprises a connector, in particular a connection thread. The connection thread can be used to screw the mixing cylinder into the bone cement system to be described below and/or to connect the mixing cylinder to a hose system via which the ready-made bone cement can be introduced into the bone. An applicator gun into which the mixing cylinder is to be clamped can be used for this activity. For ease of use of the applicator gun, the actuation rod can comprise a predetermined breakage point such that the actuation rod can break off at a defined place. For dispensing the ready-mixed bone cement, the actuation rod is pulled in the direction of the plunger system until the mixing cylinder touches against the plunger system. The plunger system, including the mixing cylinder that touches against it in front of it, can be pressed into the mixing cylinder by then breaking off the actuation rod.

In order to fill the bone cement powder into the interior of the mixing cylinder, it has proven to be advantageous if the sterilization plunger comprises a sealable, in particular a reversibly sealable, opening. This filling opening enables easy introduction of the bone cement powder into the mixing cylinder without having to remove the plunger system from the mixing cylinder. This achieves a reduction of the effort involved in filling the device according to the invention.

Moreover, it has also proven to be advantageous if the sterilization plunger and/or the sealing plunger comprise(s) at least one guide that serves for support with respect to the actuation rod. The guide prevents either of the plungers of the plunger system from becoming jammed inside the mixing cylinder. Such jamming may occur, in particular, when the sealing plunger is driven along the actuation rod in order to be applied onto the sterilization plunger. It is also advantageous if the plunger system and/or the sterilization plunger and/or the sealing plunger comprise(s) at least one sealing member in order to achieve sealing with respect to the mixing cylinder. The sealing plunger is to seal the mixing cylinder in a gas-tight manner. In addition, it is planned to have the sterilization plunger allow only particles smaller than 5 μm to flow into the mixing cylinder. To meet this requirement, it has proven advantageous if a sealing member comprises a seal on an external surface that contacts the mixing cylinder. The sealing member can, for example, be a rubber gasket that prevents ambient air from flowing into the interior of the mixing cylinder that is under a vacuum.

Another advantageous embodiment of the device according to the invention is characterized in that the plunger system and/or the sterilization plunger and/or the sealing plunger comprise(s) at least one vacuum connection. The vacuum connection can be used to connect the device to a vacuum pump. The vacuum pump then generates the negative pressure that is to be present in the mixing cylinder. As shall be described in more detail below, the negative pressure causes the binding agent, in particular the monomer, to flow into the bone cement powder. Arranging the vacuum connection in the plunger system has proven particularly advantageous due to the easy accessibility.

The object defined above is also met by a bone cement system having a device for mixing and dispensing bone cement, a reservoir for a binding agent, in particular a monomer, and a base, wherein the base stores the device and the reservoir. The device here comprises a mixing cylinder, in which a mixing plunger is arranged, wherein the mixing plunger can be moved axially by an actuation rod guided out from a first cylinder end in a sealed manner, an axially movable two-part plunger system is arranged in the region of the first cylinder end, wherein the plunger system comprises a sterilization plunger and a sealing plunger, a sterilization plunger and the sealing plunger are separately axially movable on the actuation rod, the sterilization plunger seals the mixing cylinder in a gas-permeable manner, and the sealing plunger seals the mixing cylinder in a gas-tight manner.

In this context, features and details that have been described in relation to the device shall also apply in relation to the bone cement system, and vice versa, since the bone cement system includes the device according to the invention having the plunger system with the two-part design according to the invention. In this context, the plunger system is characterized in that the sterilization plunger seals the mixing cylinder in a gas-permeable manner in order to facilitate rinsing of a bone cement powder with a sterilization agent, and the sealing plunger seals the mixing cylinder in a gas-tight manner in order to facilitate rinsing of the bone cement powder with a binding agent, in particular a monomer.

An advantageous embodiment of the bone cement system according to the invention is characterized in that the base comprises a coupling means for a non-positive and/or positive fit connection to the device, in particular to a dispensing opening of the device. The base serves to store both the device according to the invention and the reservoir for the binding agent. The device according to the invention and the reservoir can be arranged at and/or on the base as some kind of foundation of the bone cement system. Since the device according to the invention is also to be used for dispensing the bone cement, it is advantageous if the device is reversibly separable from the base. This can be attained by the coupling element according to the invention. The coupling element advantageously is a thread onto which the dispensing opening of the device can be screwed. This provides a secure connection between the base and the device.

Moreover, it is advantageous if the reservoir stores a reservoir container for the binding agent, in particular the monomer. For production of the bone cement, the binding agent, in particular the monomer, must be introduced into the bone cement powder. The bone cement then hardens after a certain period of time. It is therefore obvious that the bone cement cannot be delivered such as to be in the device and ready for dispensing. It is therefore necessary for the bone cement powder and the binding agent, in particular the monomer, to be stored separately until shortly before dispensing of the bone cement. It is therefore expedient if the reservoir comprises a reservoir container for the binding agent, in particular the monomer. Glass containers, in particular, that are used as reservoir containers for the binding agent, in particular the monomer, have proven to be easy to disinfect. The reservoir can comprise a valve to control the inflow of the monomer. The valve controls and/or triggers the inflow of the monomer from the reservoir container into the device according to the invention.

For the binding agent, in particular the monomer, to be able to flow from the reservoir into the device, the base comprises a conveyor. The conveyor can, in particular, be a capillary. The binding agent, in particular the monomer, flows from the reservoir container through the valve and the conveyor into the device, in particular into the mixing cylinder. There, the binding agent, in particular the monomer, is mixed with the bone cement powder in order to form the bone cement.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
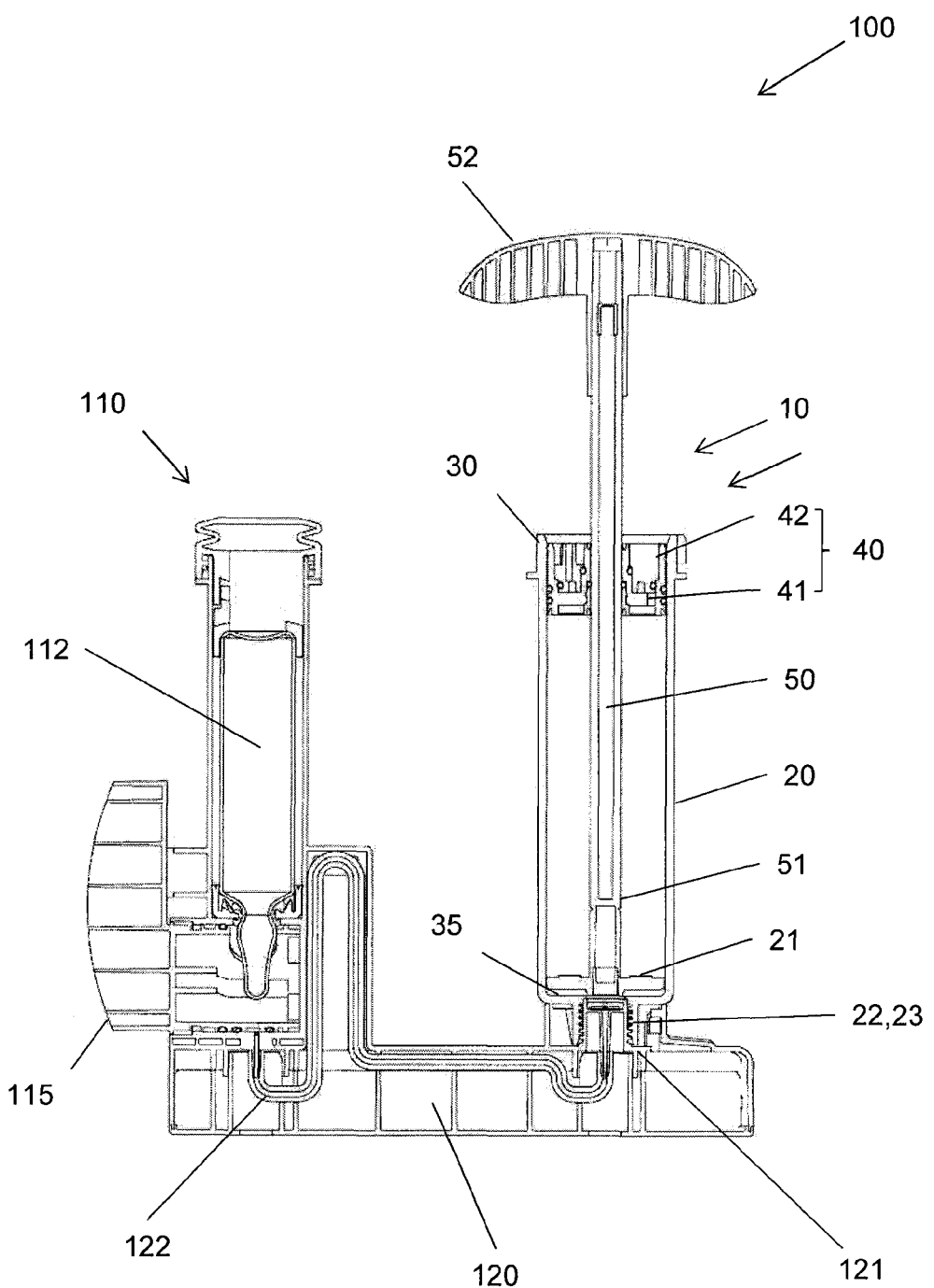
FIG. 1 is a schematic sectional view of a bone cement system according to an embodiment of the invention.

FIG. 1 shows a bone cement system 100 according to an embodiment of the invention. The bone cement system 100 comprises a device for mixing and dispensing bone cement. The device 10 is stored on a base 120 in the exemplary embodiment shown. The base 120 also carries a reservoir 110 for a binding agent, in particular a monomer. The bone cement system 100 serves for bone cement mixing. For this purpose, bone cement powder is filled into a mixing cylinder 20 of the device 10. The bone cement powder can subsequently be mixed with the binding agent, in particular the monomer, in order to form bone cement. Hereinafter, reference shall be made only to the use of the monomer though this shall not be construed as a limitation of the scope of the invention. It has proven to be a disadvantage of known bone cement systems that the disinfected bone cement systems are exposed again to their surroundings shortly before the monomer and the bone cement powder are combined, which may allow impurities, in particular germs, to enter into the bone cement powder. This disadvantage is overcome by the device 10 according to an embodiment of the invention as well as the bone cement system 100 disclosed herein.

The device 10 according to one embodiment of the invention for mixing and dispensing bone cement comprises a mixing cylinder 20. An actuation rod 50 that can be moved axially by a handle 52 is arranged in the mixing cylinder 20. As shown, the actuation rod 50 comprises on one end a mixing plunger 21 that can be used to combine the bone cement powder and the monomer. A plunger system 40 is arranged at a first cylinder end 30. The actuation rod 50 is guided through the plunger system 40 in a sealed manner. The special feature of the device 10 according to the invention is that the plunger system 40 is axially movable and consists of two parts. The plunger system 40 comprises a sterilization plunger 41 and a sealing plunger 42.

Figure 2:
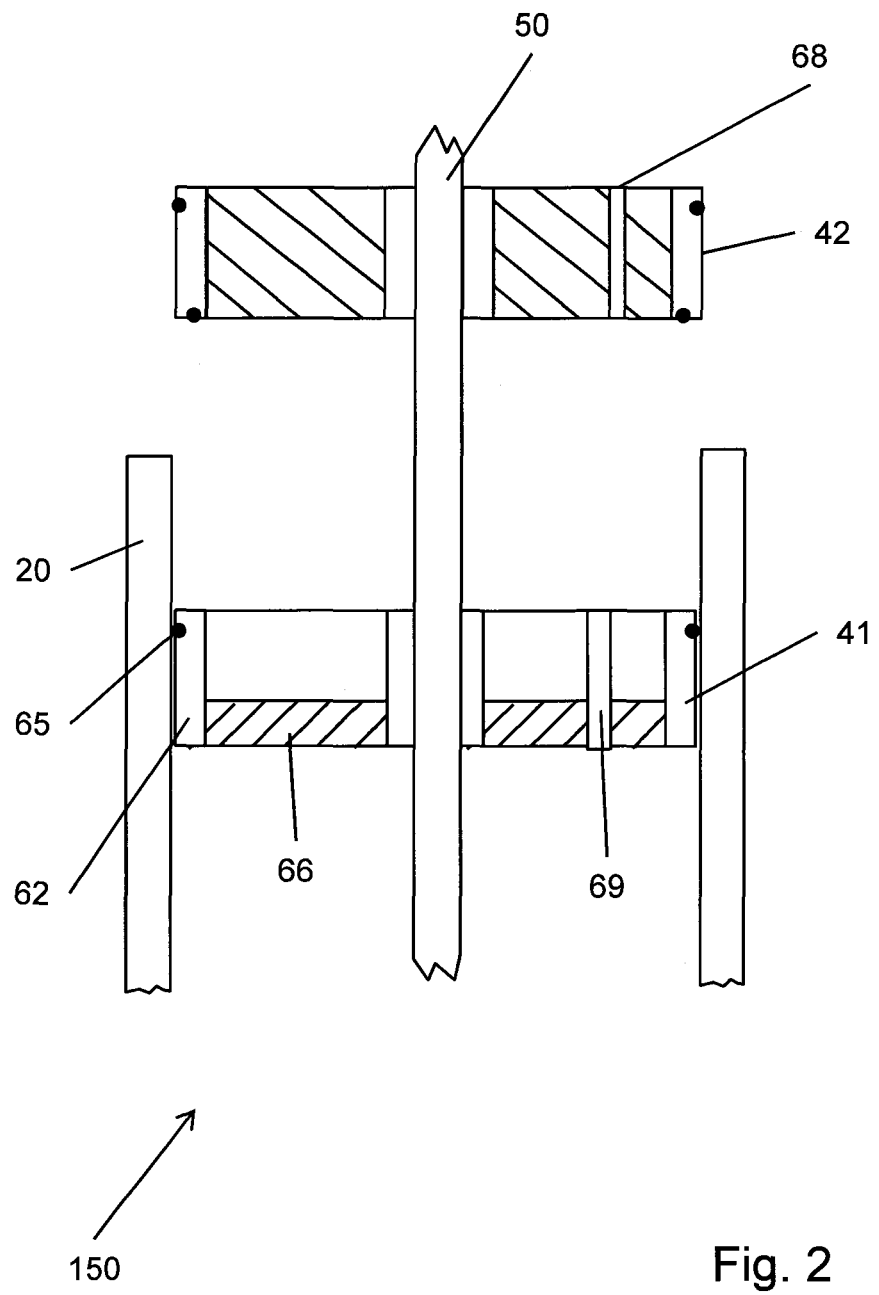
FIG. 2 is a schematic sectional view of a plunger system according to an embodiment of the invention in a sterilization position.
Figure 3:
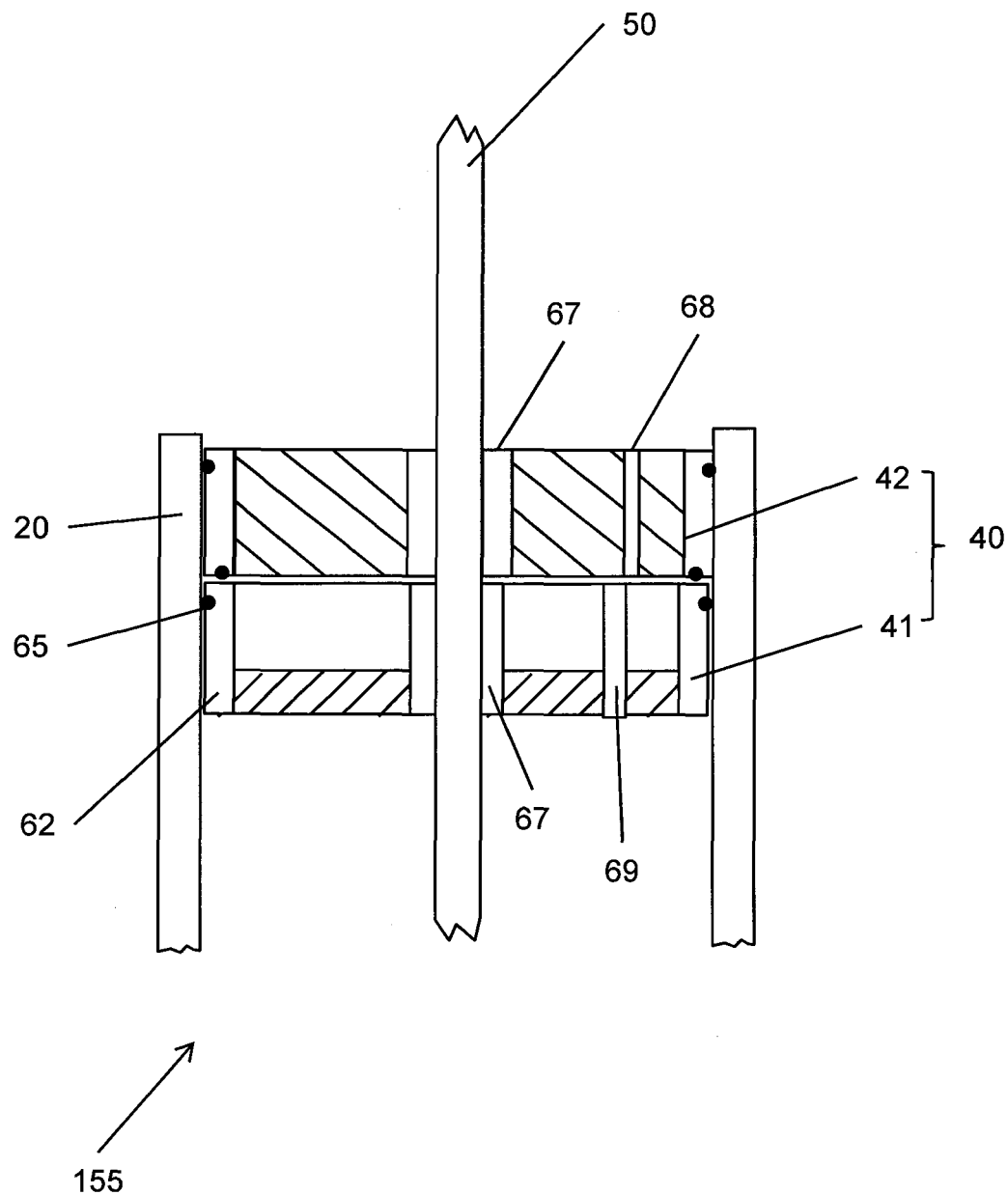
FIG. 3 is a schematic sectional view of the plunger system according to an embodiment of the invention in a mixing position.

FIGS. 2 and 3 are to illustrate the use of the two-part plunger system 40. Prior to delivery of the bone cement system 100, the manufacturer fills the mixing cylinder 20 of the device 10 with bone cement powder. Subsequently, the gas-permeable sterilization plunger 41 is inserted into the mixing cylinder 20. The resulting sterilization position 150 is shown in FIG. 2. In the sterilization position 150, the sealing plunger 42 is not inserted into the mixing cylinder 20, but rather it is shifted on the actuation rod 50 in the direction of the handle 52. In the sterilization position 150, the manufacturer can sterilize the bone cement, the device 10, and the bone cement system 100 with a fluid. Preferably, ethylene oxide is used for sterilization. The ethylene oxide can flow into the mixing cylinder through the gas-permeable sterilization plunger and rinse the bone cement powder. The sterilization plunger 41 comprises a grid-like structure 66. The grid-like structure 66 permits the inflow of the sterilization gas into the mixing cylinder 20. Advantageously, the grid-like structure 66 permits only the inflow of particles that are smaller than 5 μm. This prevents impurities from flowing into the bone cement powder.

After sterilization of the bone cement system and/or the device, the latter is usually packaged and shipped to the medical user. In the scope of a surgery, the medical user can then take the bone cement system 100 and/or the device 10 out of the package. In order to mix the bone cement powder with the monomer, the device 10 is transferred from the sterilization position to a mixing position 155 that is shown in FIG. 3. In the mixing position 155, the second part of the plunger system 40—the sealing plunger 42—is shifted axially on the actuation rod 50 in the direction of the mixing cylinder 20. The sealing plunger 42 can be plugged onto the sterilization plunger. For this purpose, both plungers 41, 42 can comprise corresponding means in order to effect a non-positive and/or positive fit connection. Following the transfer of the plunger system 40 into the mixing position 155, the device 10 is connected to a vacuum system. For this purpose, the plunger system 40 comprises a vacuum connection 68. The vacuum connection 68 is arranged in the sealing plunger 42. Since the sterilization plunger 41 is gas-permeable, there is no need for a vacuum connection. The vacuum connection 68 is used to establish a negative pressure in the interior of the mixing cylinder 20.

As illustrated in FIG. 1, reservoir 110 is also a part of the bone cement system. Reservoir 110 stores a reservoir container 112 for the monomer. The outflow of the monomer from the reservoir container 112 can be controlled and/or triggered via a valve 115. Advantageously, the reservoir container 112 is a glass container that is opened in its head region by the valve 115. The monomer then flows through a conveyor 122 from the reservoir container 112 into the mixing cylinder 20. The transfer flow of the monomer is increased since a negative pressure is present in the mixing cylinder 20. The bone cement powder and the monomer can then be mixed easily and simply by the actuation rod and the mixing plunger 21.

After mixing is completed, the device 10 can be unscrewed from the base 120. For this purpose, the base 120 comprises a coupler 121 that acts in concert with a connector 22 of the mixing plunger. After separation of the device 10 from the base 120 is effected, the actuation rod 50 is shifted axially such that the mixing plunger 21 comes to rest against the plunger system 40. Subsequently, the actuation rod can be snapped off at the predetermined breakage point 51. The device 10 can now be integrated into a cementing gun. Actuation of the cementing gun moves a toothed rack with collar in the direction of the plunger system 40. Advantageously, the plunger system 40 can be used not only for bone cement sterilization and mixing, but also for dispensing the bone cement. For this purpose, the plunger system 40 is designed to be axially movable. For this purpose, the plunger system 40 can be moved axially into the mixing cylinder 20. This allows the bone cement formed by mixing from bone cement powder and monomer to be dispensed through a dispensing opening 23.

Both the sterilization plunger 41 and the sealing plunger 42 of the plunger system 40 according to this embodiment of the invention comprise sealing members 65 that prevent ambient influences from flowing into the interior of the mixing cylinder. Moreover, the two plungers 41, 42 of the plunger system 40 comprise guides 67 that serve for support with respect to the actuation rod 50. Jamming of the two plungers 41, 42 is thereby prevented. In order for the sterilization plunger 41 not to have to be removed from the mixing cylinder 20 when the bone cement powder is filled into the device 10, the sterilization plunger 41 can comprise a filling opening 69. The bone cement powder can be filled into the interior of the mixing cylinder 20 through the filling opening, which in particular is reversibly sealable.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A device (10) for mixing and dispensing bone cement, the device comprising:
   a mixing cylinder (20) in which a mixing plunger (21) is arranged, the mixing plunger (21) being axially movable by an actuation rod (50) guided out in a sealed manner at a first cylinder end (30),
   a sealing plunger (42) arranged in a region of the first cylinder end (30) being axially movable on the actuation rod (50) and configured to seal the mixing cylinder (20) in a gas-tight manner,
   a sterilization plunger (41) comprising a gas-permeable grid, arranged in the region of the first cylinder end (30) between the mixing plunger (21) and the sealing plunger (42), being axially movable on the actuation rod (50) separately from the sealing plunger (42) and configured to seal the mixing cylinder (20) in a gas-permeable manner, wherein the gas-permeable grid is adapted to allow only particles smaller than 5 μm to pass therethrough; wherein the sterilization plunger (41) and the sealing plunger (42) form a two-part plunger system (40) having a sterilization position (150) and a mixing position (155), wherein in the sterilization position (150) the sterilization plunger (41) seals the mixing cylinder (20) in the gas-permeable manner and the sealing plunger (42) does not seal the mixing cylinder (20) in the gas-tight manner, such that the plunger system (40) enables a sterilization agent to both flow into the mixing cylinder (20) to rinse bone cement powder therein and exit the mixing cylinder (20), and in the mixing position (155), sealing plunger (42) seals the mixing cylinder (20) in the gas-tight manner, and allows the bone cement powder to be rinsed by a binding agent.

2. The device (10) according to claim 1, wherein the plunger system (40) surrounds the actuation rod (50).

3. The device (10) according to claim 1, wherein the sealing plunger (42) can be plugged onto the sterilization plunger (41).

4. The device (10) according to claim 1, wherein the plunger system (40) can be pushed axially into the mixing cylinder (20) in order to dispense a bone cement prepared by mixing from the bone cement powder and the binding agent through a dispensing opening (23).

5. The device (10) according to claim 4, wherein the dispensing opening (23) comprises a connection thread.

6. The device (10) according to claim 1, wherein the actuation rod (50) has a predetermined breakage point (51).

7. The device (10) according to claim 1, wherein the sterilization plunger (41) has a reversibly sealable filling opening (69).

8. The device (10) according to claim 1, wherein at least one of the plunger system (40), the sterilization plunger (41) and the sealing plunger (42) has at least one vacuum connection (68).

9. A bone cement system (100) comprising (i) a device (10) for mixing and dispensing bone cement according to claim 1, said device further comprising a dispensing opening (23), (ii) a reservoir (110) for storing a binding agent therein, and (iii) a base (120), wherein configured to carry each of the reservoir (110) and the device (10), and to connect outflow of the reservoir (110) with the dispensing opening of the mixing cylinder (20) of the device (10).

10. The bone cement system (100) according to claim 9, wherein the base (120) comprises a coupler (121) for a non-positive and/or positive fit connection to the device (10).

11. The bone cement system (100) according to claim 10, wherein the coupler (121) connects to the dispensing opening (23) of the device (10).

12. The bone cement system (100) according to claim 9, wherein the reservoir (110) stores a reservoir container (112) for the binding agent.

13. The bone cement system (100) according to claim 12, wherein the reservoir (110) has a valve (115) to control and/or trigger an outflow of the binding agent from the reservoir container (112).

14. The bone cement system (100) according to claim 9, wherein the base comprises a conveyor (122) for flow of the binding agent from the reservoir container (112) into the mixing cylinder (20) of the device (10).

* * * * *